US008107070B2

(12) United States Patent
Zhao et al.

(10) Patent No.: US 8,107,070 B2
(45) Date of Patent: Jan. 31, 2012

(54) METHODS OF MELAMINE DETECTION AND QUANTIFICATION

(75) Inventors: Yiping Zhao, Statham, GA (US); Xiaobing Du, Chongqing (CH)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 12/802,684

(22) Filed: Jun. 11, 2010

(65) Prior Publication Data

US 2011/0069308 A1  Mar. 24, 2011

Related U.S. Application Data

(60) Provisional application No. 61/186,062, filed on Jun. 11, 2009.

(51) Int. Cl.
*G01J 3/44* (2006.01)
(52) U.S. Cl. ......................................................... 356/301
(58) Field of Classification Search .................. 356/301, 356/72–73; 977/810–950
See application file for complete search history.

(56) References Cited

U.S. PATENT DOCUMENTS

| 7,274,458 | B2 | 9/2007 | Perez et al. | |
| 7,361,410 | B2 | 4/2008 | Zhang et al. | |
| 7,443,489 | B2 | 10/2008 | Natan | |
| 7,465,681 | B2 * | 12/2008 | Hart et al. | 438/788 |
| 7,485,471 | B1 | 2/2009 | Sun et al. | |
| 2010/0085564 | A1 * | 4/2010 | Guo et al. | 356/301 |

OTHER PUBLICATIONS

Koglin, et al., "Adsorption and Displacement of Melamine at the Ag/Electrolyte Interface Probed by Surface-Enhanced Raman Microprobe Spectroscopy", J. Phys. Chem 1996, 100, 5078-5089.
Turley, "Fatal Food Fraud", Society of Chemical Industry, C&I Magazine, Issue 8, Apr. 27, 2009.
Hanwen, et al., "The Research Advancement for Analytical Methodology of Melamine and Related Analogues in Environment and Foods", Aug. 1, 2009, vol. 11, No. 8, p. 37.
Mermelstein, "Analyzing for Melamine," Food Technology, Feb. 2009.
Liu, et al., "Potential of SERS for Rapid Detection of Melamine and Cyanuric Acid Extracted from Milk",Springer Science+Business Media, LLC, Jul. 29, 2009.
Cheng, et al., "Screening Melamine Adulterant in Milk Powder with Laser Raman Spectrometry", Journal of Food Composition and Analysis 23 (2010) 199-202.
He, et al., "A New Approach to Measure Melamine, Cyanuric Acid, and Melamine Cyanurate Using Surface Enhanced Raman Spectroscopy Coupled with Gold Nanosubstrates", Springer Science+Business Media, LLC, Nov. 16, 2007, pp. 66-71.
Lin, et al., "Detection of Melamine in Gluten, Chicken Feed, and Processed Foods Using Surface Enhanced Raman Spectroscopy of HPLC." Toxicology and Chemical Food Safety, vol. 73, No. 8, 2008—Journal of Food Science, pp. 129-135.

* cited by examiner

*Primary Examiner* — Tarifur Chowdhury
*Assistant Examiner* — Abdullahi Nur
(74) *Attorney, Agent, or Firm* — Thomas, Kayden, Horstemeyer & Risley, LLP

(57) ABSTRACT

Embodiments of the present disclosure relate to methods of melamine detection and quantification. In particular, embodiments of the present disclosure include the detection of very low concentrations of melamine using silver nanorod array substrates fabricated by oblique angle deposition (OAD) technique.

15 Claims, 11 Drawing Sheets
(7 of 11 Drawing Sheet(s) Filed in Color)

METHODS OF MELAMINE DETECTION AND QUANTIFICATION

CROSS-REFERENCE TO RELATED APPLICATION

This application claims priority to U.S. provisional application entitled "Methods of Melamine Detection and Quantification" having Ser. No. 61/186,062 filed on Jun. 11, 2009, which is entirely incorporated herein by reference.

BACKGROUND

Melamine (2,4,6-triamino-1,3,5-triazine) is mainly used in the synthesis of melamine resins, the latter is widely used in industry for its heat tolerance to produce kitchenware, flame retardants, commercial filters, etc. Melamine was also found as a metabolite of the pesticide cyromazine in plants, goats, hens and rats and is used in some fertilizers. Due to the widespread use of melamine, trace levels may be detected in food, although it is not a kind of food stuffs and additives, and it is forbidden to add to any foods by authorities of any country. Although melamine has a low acute toxicity, it is still thought of as the factor which causes bladder stones, and experimental studies have also shown that combination with cyanuric acid leads to crystal formation and subsequently causes kidney stones.

The compound is an indirect food additive, and there is an increasing concern about the detection of melamine in foods following the pet food incident in 2007 and melamine-tainted formula incident in 2008, which involved the intentional adulteration of protein ingredients used in milk products with melamine to make the products appear to contain a higher protein content than they actually did.

After the pet food incident in 2007 and melamine-tainted formula incident in 2008, many standards were stipulated and amended by different countries and areas. On Nov. 29, 2008, the U.S. Food and Drug Administration (FDA) set a threshold of 1 part per million of melamine in formula, provided cyanuric acid is not also present, instead of the old announcement of no safe level of melamine in baby formula. For all other foods, only amounts less than 2.5 parts per million (ppm) are risk free. In China, 2.5 mg per one kilogram (mg/kg) standard for adult foods and 1.0 mg per one kilogram (mg/kg) for formula has been set. This safety standard is currently widely accepted around the world to address situations in which the chemical accidentally comes into contact with circumstances. In fact, the concentrations of melamine detected in contaminated formulas were extraordinarily high, as much as 2,500 parts per million.

At present, many detection methods of melamine have been reported. The popular methods are HPLC-MS, GC-MS, and HPLC-UV, and ELISA, Et al. Although HPLC, GC and GC-MC are fast and accurate, they are costly. ELISA is limited with its accuracy. Simple, accurate, and rapid detection methods are still urgently needed for the short shelf-time of fresh milk.

SUMMARY

Embodiments of the present disclosure relate to methods of melamine detection and/or quantification.

Briefly described, embodiments of the present disclosure can include a method of detecting melamine in a sample comprising providing a surface enhanced Raman spectroscopy (SERS) substrate, where the SERS substrate comprises a Ag nanorod array substrate, exposing the sample to the substrate, and obtaining a unique SERS spectrum for the melamine.

Briefly described, embodiments of the present disclosure can include a method of detecting and quantifying melamine in a sample comprising providing a surface enhanced Raman spectroscopy (SERS) substrate, where the SERS substrate comprises a Ag nanorod array substrate, exposing the sample to the substrate, obtaining a unique SERS spectrum for the melamine, and analyzing the unique SERS spectrum to quantify the melamine.

BRIEF DESCRIPTION OF THE DRAWINGS

Many aspects of this disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

The patent or application file contains at least one drawing executed in color. Copies of this patent or patent application publication with color drawing(s) will be provided by the Office upon request and payment of the necessary fee.

DETAILED DESCRIPTION

Figure 1:
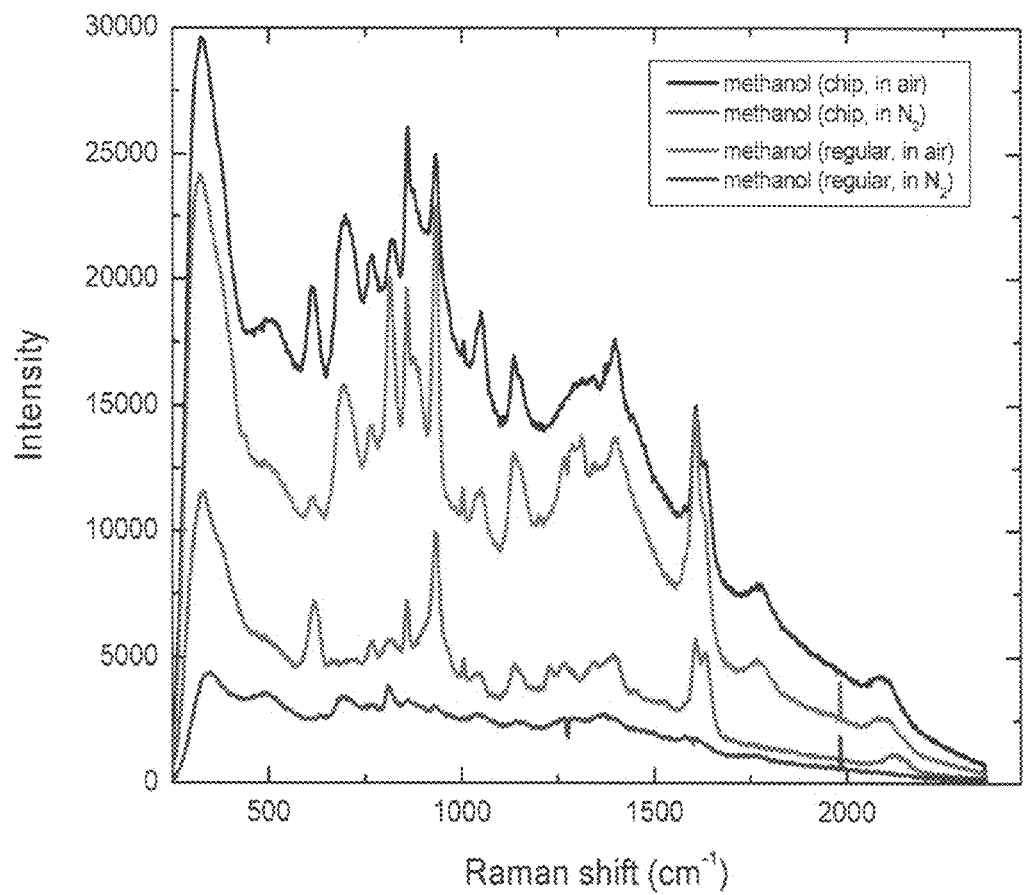
FIG. 1 is a graph that illustrates the effect of methods of Sample application.
Figure 2:
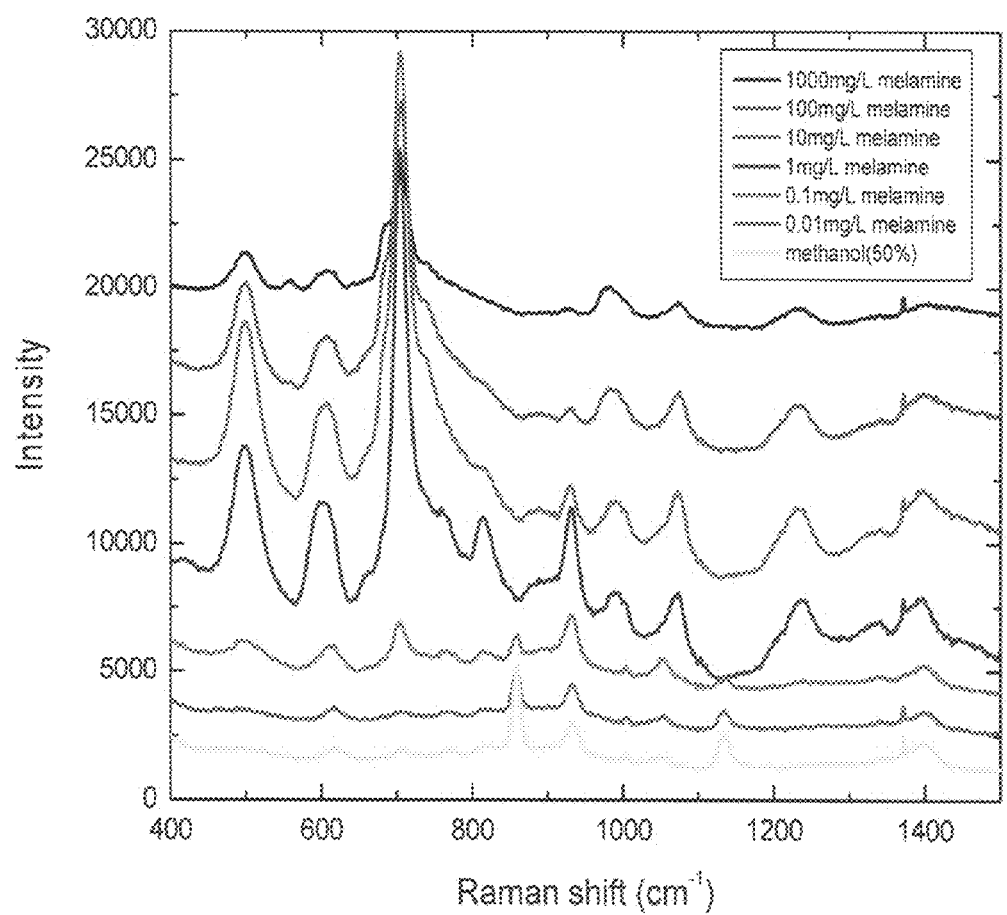
FIG. 2 is a graph that illustrates the average spectra of different concentrations of melamine.
Figure 3:
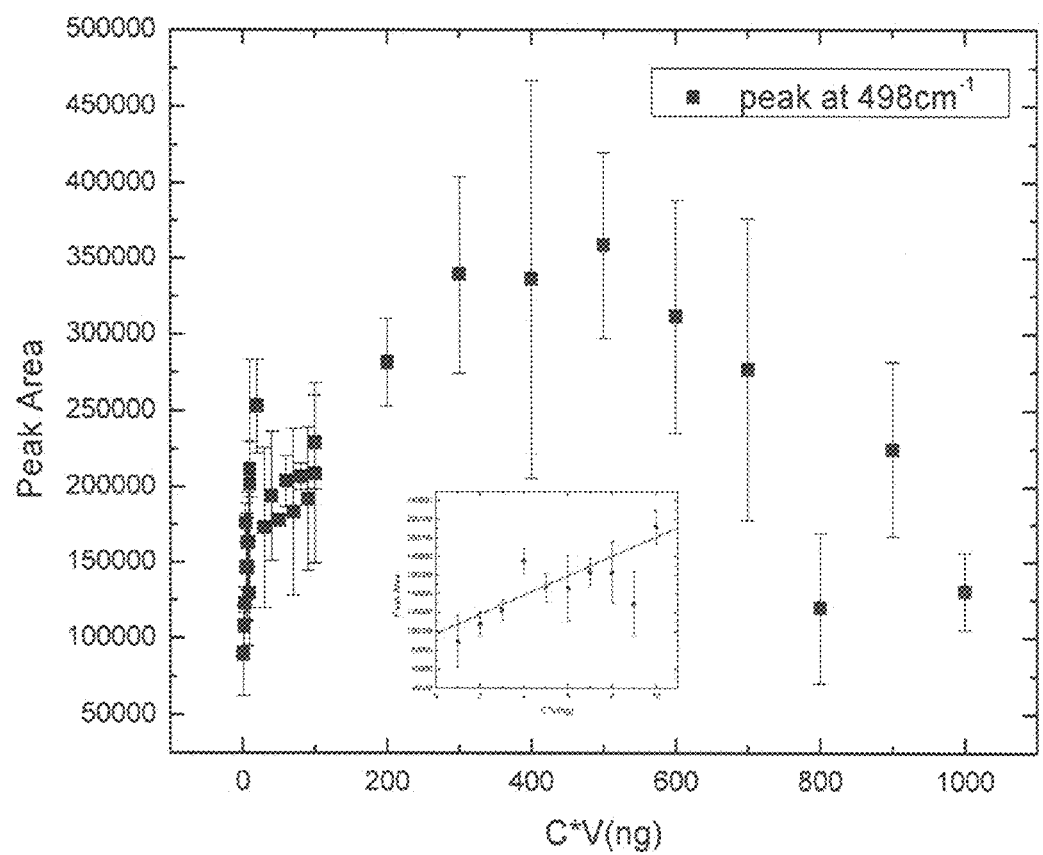
FIG. 3 is a graph that illustrates the relationship between the value of concentration of melamine by volume of sample and the area of peak at 498 cm$^{-1}$; C—concentration of melamine; V—volume of sample.
Figure 4:
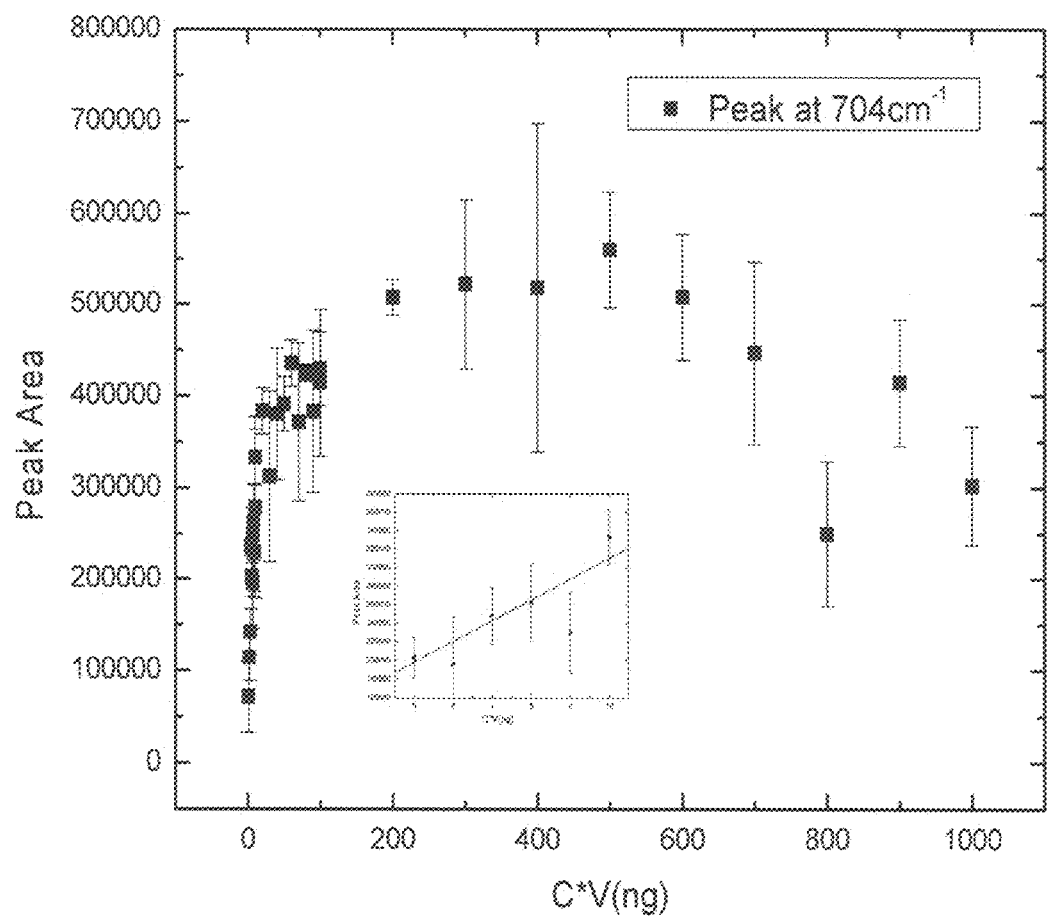
FIG. 4 is a graph that illustrates the relationship between the value of concentration of melamine by volume of sample and the area of peak at 704 cm$^{-1}$.
Figure 5:
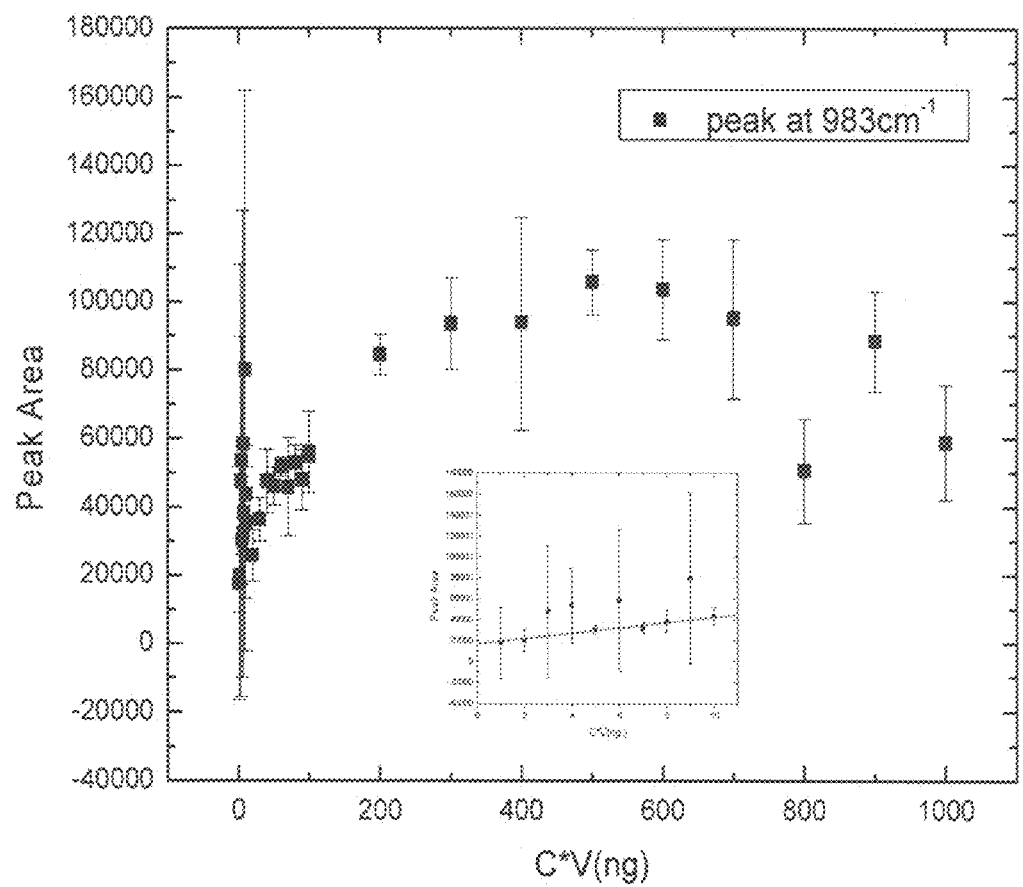
FIG. 5 is a graph that illustrates the relationship between the value of concentration of melamine by volume of sample and the area of peak at 983 cm$^{-1}$.
Figure 6:
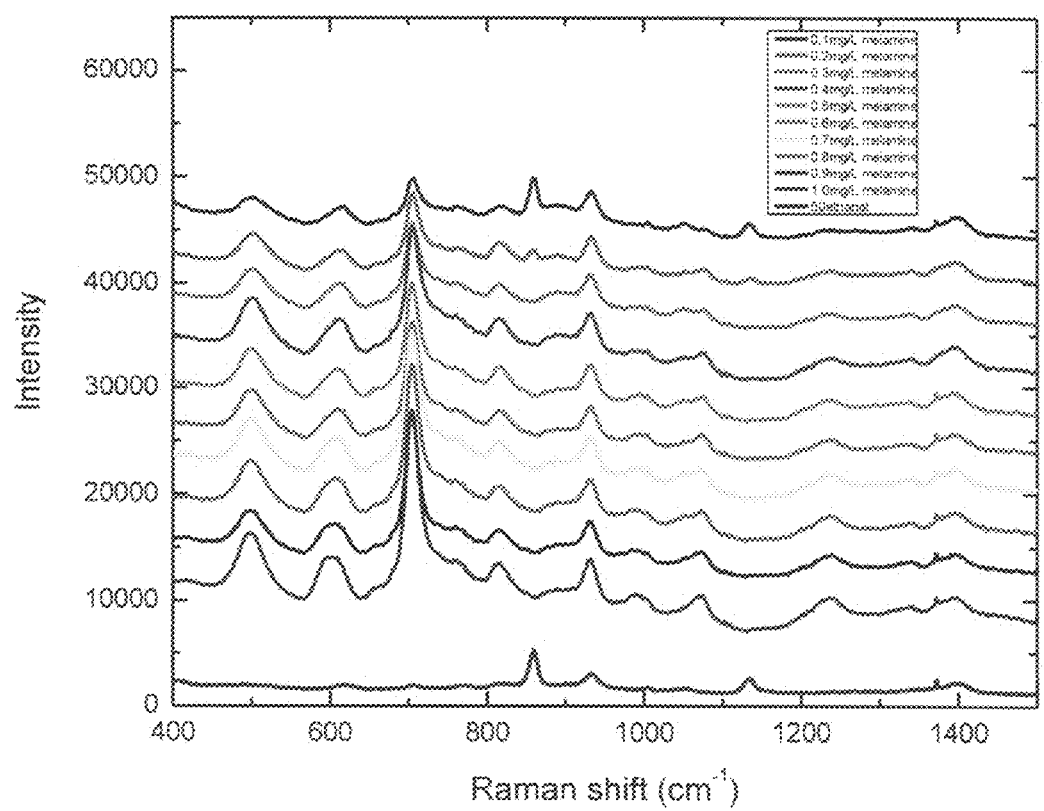
FIG. 6 is a graph that illustrates the lowest concentration of melamine which can be detected (the concentrations of melamine are from 1 mg/L to 0.1 mg/L). The limit of detection of melamine is 0.1 mg/L, or 0.1 mg/kg.
Figure 7:
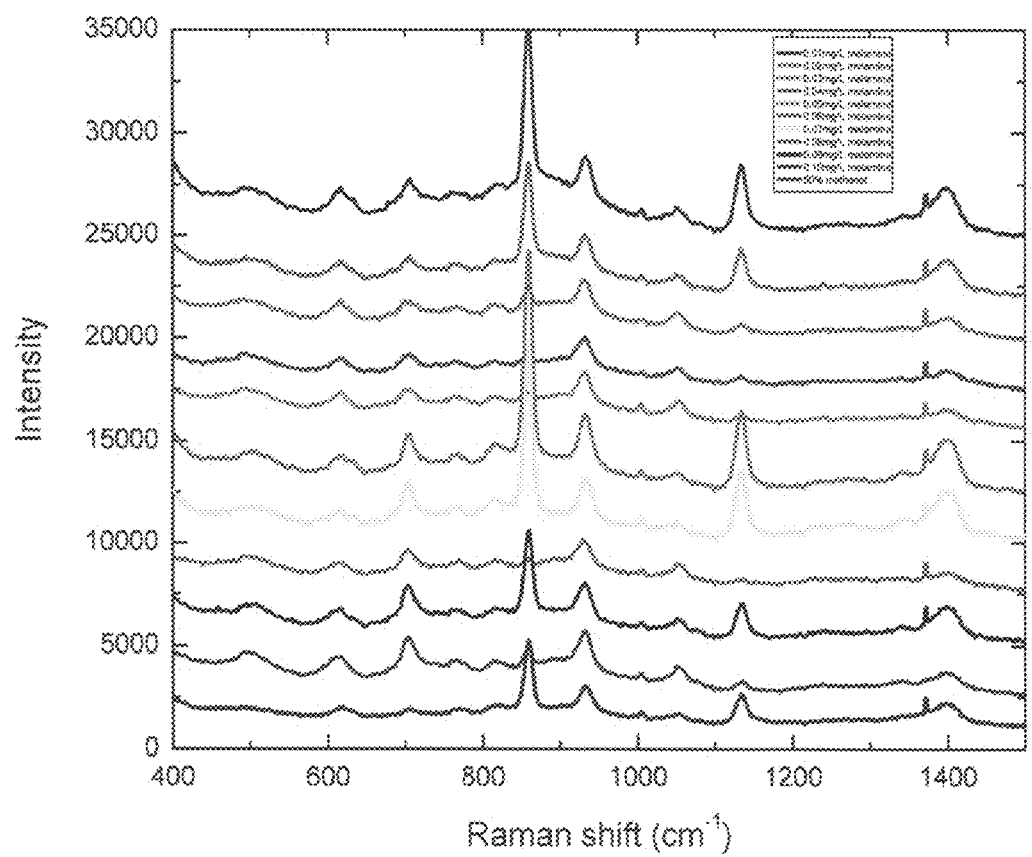
FIG. 7 is a graph that illustrates the lowest concentration of melamine which can be detected (the concentrations of melamine are from 0.1 mg/L to 0.01 mg/L).

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Discussion

In accordance with the purpose(s) of the present disclosure, as embodied and broadly described herein, embodiments of the present disclosure, in one aspect, relate to methods of melamine detection and/or quantification. In particular, embodiments of the present disclosure include the detection of very low concentrations of melamine using silver nanorod array substrates fabricated by oblique angle deposition (OAD) technique.

Melamine (2,4,6-triamino-1,3,5-triazine) is used to synthesize melamine resins, which are widely used in industry for heat tolerance to produce kitchenware, flame retardants, commercial filters, etc. Melamine is also found as a metabolite of the pesticide cyromazine in plants, goats, hens and rats and is used in some fertilizers. Due to the widespread use of melamine, trace levels may be detected in food.

Although melamine has a low acute toxicity, it is still thought to cause bladder stones, and experimental studies have shown that combination with cyanuric acid leads to crystal formation, subsequently causing kidney stones. There is an increasing concern about the detection of melamine in foods following the pet food incident in 2007 and melamine-tainted formula incident in 2008.

Embodiments of the present disclosure includes methods of detecting melamine in a sample comprising: providing a surface enhanced Raman spectroscopy (SERS) substrate where the SERS substrate comprises a Ag nanorod array substrate, exposing the sample to the substrate, and obtaining a unique SERS spectrum for the melamine (e.g., three prominent peaks at 498 $cm^{-1}$, 704 $cm^{-1}$, and 983 cm).

In an embodiment, the nanostructures (e.g., nanorods) can be fabricated of one or more materials such as, but not limited to, a metal, a metal oxide, a metal nitride, a metal oxynitride, a metal carbide, a doped material, a polymer, a multicomponent compound, a compound (e.g., a compound or precursor compound (organic or inorganic compound) including a metal, a metal oxide, a metal nitride, a metal oxynitride, a metal carbide, a doped material), and combinations thereof. The metals can include, but are not limited to, silver, nickel, aluminum, silicon, gold, platinum, palladium, titanium, copper, cobalt, zinc, other transition metals, composites thereof, oxides thereof, nitrides thereof, silicides thereof, phosphides ($P^{3-}$) thereof, oxynitrides thereof, carbides thereof, and combinations thereof.

In an embodiment of the SERS substrate of the present disclosure, the nanostructure can be a nanorod. In particular embodiments, the nanorod is formed in a uniform and aligned array on the substrate. The nanorod can have the dimensions and characteristics as described below. In particular, the nanorods (e.g., silver, nickel, silicon, and titanium oxide) are disposed on a planar substrate, such a glass or silicon slide or disk, or a non-planar substrate, such as an optical fiber, or other cylindrically symmetric substrates.

In embodiments of the SERS substrates of the present disclosure, the nanorods also have a tilt angle, β, formed between the nanostructure 102 and the substrate 106. The angle β is less than 90°, particularly from about 0° to about 50°, and in preferred embodiments can be from about 5° to about 20°, from about 15° to about 30°, and from about 25° to about 40°. The conditions and the materials used to prepare the nanostructure 102 can be used to determine/select the tilt angle. The tilt angle is important in creating SERS enhancement factors with sufficient sensitivity to detect binding of an analyte of interest to the SERS sensors of the present disclosure.

In an embodiment, an angle, β, is formed between the nanorod and the substrate, and the angle can be about 30° to 75°. In an embodiment, the angle can be about 0° to 90°.

In an embodiment, the nanorods can be formed using a modified oblique angle deposition (OAD) technique/system (additional details are described in U.S. Pat. No. 7,658,991 B2, which is incorporated herein by reference). For example, the OAD system can include a two-axis substrate motion system in a physical vapor deposition (PVD) device (e.g., thermal evaporation, e-beam evaporation, sputtering growth, pulsed laser deposition, and the like) that operates at temperatures lower than the melting point of the material used to form the nanorods. In an embodiment, the substrate motion system provides two rotation movements: one is the polar rotation, which changes angle between the substrate surface normal and the vapor source direction, and one is the azimuthal rotation, where the sample rotates about its center axis of rotation (e.g., normal principle axis).

Embodiments of the OAD system can include a physical vapor deposition (PVD) device, such as thermal evaporation, e-beam evaporation, molecular beam epitaxy (MBE), sputtering growth, pulsed laser deposition, combinations thereof, and the like, to form the nanorods.

In an embodiment, the nanorods are in an array, and the array of nanorods can be defined as having a distance of about 10 to 30 nm, about 10 to 60 nm, about 10 to 100 nm, about 10 to 150 nm, or about 10 to 200 nm, between each of the nanostructures. Alternatively, the array of nanorods can be defined as having an average density of about 11 to 2500/μm$^2$.

The length is the largest dimension of the nanorod and is the dimension extending from the substrate. The nanorod can have a length of about 10 nm to 5000 nm, about 10 nm to 4000 nm, about 10 nm to 3000 nm, about 10 nm to 2000 nm, about 10 nm to 1000 nm, about 10 nm to 500 nm, about 10 nm to 250 nm, about 10 nm to 100 nm, or about 10 nm to 50 nm. The length depends, at least in part, upon the deposition time, deposition rate, and the total amount of evaporating materials. The diameter is the dimension perpendicular to the length. The diameter of the nanorod is about 10 to 30 nm, about 10 to 60 nm, about 10 to 100 nm, or about 10 to 150 nm. One or more of the dimensions of the nanorod could be controlled by the deposition conditions and the materials.

It should also be noted that the nanostructure could have multiple layers of different materials or alternating materials. The materials can be any combination of the materials described herein.

A more detailed description of the SERS substrate may be found in U.S. Pat. No. 7,583,379 and U.S. Utility application Ser. No. 11/376,661, which are herein incorporated by reference.

Embodiments of the present disclosure can include a method of detecting melamine in a sample where the SERS substrate comprises a multi-well array substrate. In an embodiment, the multi-well array substrate comprises at least one well, where the well has a bottom surface and a side surface, and where a plurality of nanorod structures are disposed on the bottom surface. In another embodiment, the plurality of nanorod structures comprise Ag nanorod structures.

Embodiments of the present disclosure include a method of detecting melamine in a sample where the SERS substrate comprises a multi-well array substrate and where the side surface can be made of a material selected from the group consisting of: polydimethylsiloxane (PDMS), fluorinated PDMS, poly(methyl methacrylate) (PMMA), polycyclic olefin polyethylene copolymers, polycarbonate, polyalkanes, polyacrylate polybutanol co-polymers, polystyrenes, polyionomers, polybutyl terephthalate (PBT), polyamides, polyoxymethylene (POM), other acetyl resins, and a combination thereof, and the bottom surface can be made of a silicon material.

In an embodiment of the present disclosure, the wells can be a shape selected from the group consisting of: a cylindrical shape, a conical shape, a polygonal shape, and a combination thereof.

Embodiments of the present disclosure include a method of detecting and quantifying melamine in a sample comprising: providing a SERS substrate where the SERS substrate comprises a Ag nanorod array substrate, exposing the sample to the substrate, obtaining a unique SERS spectrum for the melamine, and analyzing the unique SERS spectrum to quantify the melamine. In an embodiment, an angle, β, is formed between the nanorod and the substrate, and the angle can be about 30° to 75°. In another embodiment, an angle, β, is formed between the nanorod and the substrate, and the angle can be about 0° to 90°. The angle will help to promote the SERS "hot spot" sites on the surface, and increase the enhancement of SERS signals of the molecules located in-between the nanorods.

Analysis of the unique SERS spectrum can include an analysis of the quantitative relationship between the SERS peak intensities and the mass of melamine under detection. The peak intensities increase almost linearly when the melamine concentration increases from 0.1 mg/L to 10 mg/L, and saturate when melamine concentration is larger than 50 mg/L. In an embodiment, a standard curve can be used to analyze and quantify the amount of melamine in a sample.

In an embodiment, the detectable concentration of melamine is at least as low as about 0.01 mg/L to about 0.1 mg/L (or 0.01 mg/kg to 0.1 mg/kg).

Embodiments of the present disclosure include a method of detecting and quantifying melamine in a sample where the SERS substrate comprises a multi-well array substrate. In an embodiment, the multi-well array substrate comprises at least one well, wherein the well has a bottom surface and a side surface, and wherein a plurality of nanorod structures are disposed on the bottom surface. In another embodiment, the plurality of nanorod structures comprise Ag nanorod structures.

Embodiments of the present disclosure include a method of detecting and quantifying melamine in a sample where the SERS substrate can include a multi-well array substrate such as those described above.

EXAMPLES

Ag nanorod (AgNR) array substrates were investigated to detect pure melamine dissolved in 50% methanol by surface-enhanced Raman spectroscopy (SERS). We find that sample preparation conditions have a great influence on melamine detection. When the samples are prepared under a nitrogen glove box, the SERS characteristic peak intensities of melamine at $\Delta v=497$ cm$^{-1}$, 704 cm$^{-1}$ and 983 cm$^{-1}$, are studied as functions of melamine concentration and/or the mass of melamine. The peak intensities increase almost linearly when the melamine concentration increases from 0.1 mg/L to 10 mg/L, and saturate when melamine concentration is larger than 50 mg/L. The bulk melamine limit of detection (LOD) is 0.1 mg/L, which is one order of magnitude less than the current standard. This study shows that AgNR based SERS detection can be used as a fast, highly sensitive, and quantitative detection method for melamine.

Introduction

Melamine (2,4,6-triamino-1,3,5-triazine) is a chemical substance mainly used to synthesize melamine resins, and is widely used in industry to produce kitchenware, flame retardants, commercial filters, etc., due to its excellent heat tolerance (World Health Organization. Melamine and Cyanuric acid: Toxicity, Preliminary Risk Assessment and Guidance on Levels in Food. Article Date: 3 Oct. 2008-4:00 PDT, which is herein incorporated by reference for the corresponding discussion). Melamine is also used in some fertilizers and is found as a metabolite of a pesticide, cyromazine, which can be found in plants and mammals that have ingested the pesticide (World Health Organization Food and Agriculture Organization of the United Nations. Pesticide residues in food—2006. Report of the Joint Meeting of the FAO Panel of Experts on Pesticide Residues in Food and the Environment and WHO the Core Assessment Group. FAO Plant Production and Protection Paper, 187. Rome, 3-12 Oct. 2006, which is herein incorporated by reference for the corresponding discussion). Due to the wide use of melamine, trace amounts of melamine may be detected in food, although it has been forbidden to be used as a food additive. While melamine has a low acute toxicity, it is still thought to be harmful to human health. Studies have shown that the combination of cyanuric acid and melamine leads to crystal formation and subsequently causes kidney stones (World Health Organization. Melamine and Cyanuric acid: Toxicity, Preliminary Risk Assessment and Guidance on Levels in Food. Article Date: 3 Oct. 2008-4:00 PDT; Melnick R L, Boorman G A, Haseman J K, Montali R J, Huff J. Toxicol Appl Pharmacol. 72, 2, 292 (1984); DHHS/NTP. Toxicology and Carcinogenesis Studies of Melamine (CAS No. 108-78-1) in F344/N Rats and B6C3F1 Mice (FeedStudies). Technical Rpt Series. 245, 83 (1983), which are herein incorporated by reference for the corresponding discussion). There is an increasing concern about the detection of melamine in food products following the pet food contamination incident in 2007 and melamine-tainted formula incident in China in 2008. In the melamine-tainted formula incident, milk products were adulterated to raise the nitrogen concentration in quality analysis so that the milk products could meet the material specification. In the wake of the incident, many standards have been stipulated and amended by different countries around the world to better safeguard general consumers. Both the United States and China have set a threshold of 1 part per million (ppm, or mg/kg) of melamine in formula, provided cyanuric acid is also not present. For all other foods, only amounts less than 2.5 parts per million (or mg/kg) are considered risk free (New Hope Network. FDA Sets Melamine Standard for Formula after Traces of Chemical Found in U.S. [Internet]. 2008-2009. Available from: http://nutritionbusinessjournal.com/ingredient-supply/news/12-02-fda-sets-melamine-standard-formula-traces-chemical-found-US-made-products/; The Wall Street Journal Nutrition Blogs. China Adopts New Melamine Standards. Oct. 8, 2008. Available from: http://blogs.wsj.com/chinajournal/2008/10/08/china-adopts-new-melamine-standards/, which are herein incorporated by reference for the corresponding discussion). Currently, this standard is widely accepted around the world. The new standard imposes a new challenge for fast and accurate detection of melamine in a food matrix.

Among the current detection methods of melamine, the popular methods are high performance liquid chromatography-mass spectrometry (HPLC-MS), gas chromatography-mass spectrometer (GC-MS), high performance liquid chromatography with ultraviolet detection (HPLC-UV), and enzyme-linked immunosorbent assay (ELISA) (Journal of Agricultural and Food Chemistry. 56, 17, 7593 (2008); Journal of Food Protection. 71, 3, 590 (2008), which are herein incorporated by reference for the corresponding discussion). Although HPLC, GC and GC-MS are fast and accurate, the equipment is expensive, they require specialized operators, and their field application is limited; ELISA is limited by its accuracy and long testing time (Journal of Food Protection. 71, 3, 590 (2008), which is herein incorporated by reference for the corresponding discussion). Therefore, accurate and rapid detection methods are still urgently needed, especially for short shelf-life products such as fresh milk.

Surface-enhanced Raman spectroscopy (SERS) is a novel and ultra-sensitive method for detecting chemical and biological molecules (J. Raman Spectros. 36, 485, (2005); J. Phys. Chem. B. 106, 9463 (2002); *Metallic Nanomaterials* (S. R. Kumar, Challa S, 2009). Vol. 1, WILEY-VCH p. 173-224, which are herein incorporated by reference for the corresponding discussion). The method relies on the analysis of molecules in close proximity to a roughened noble metal surface, which has been shown to enhance the intensity of the Raman signal by more than six orders of magnitude. The limit of detection (LOD) of SERS can be as low as single molecule detection (Id.). Although there are a few reports on Raman spectroscopic characterizations of melamine, most of them mainly focus on using the normal Raman spectra to distinguish a high concentration of melamine (Food Quality. 1, 2, 66 (2008); Holzforschung. 59, 2, 210 (2005); Lenzinger Berichte. 83, 13 (2004); Journal of Food Science. 73, 8, 129 (2008); Composites Part A: Applied Science and Manufacturing. 36, 1, 95 (2005); Talanta. 72, 2, 847 (2007); Acta Chimica Slovenica. 50, 2, 239 (2003); Molecular physics. 103, 24, 3309 (2005); Appied Spectroscopy 48, 4, 535 (1994); Journal of Physics and Chemistry of Solids. 64, 11, 2169 (2003); Analytical Chemistry. 79, 20, 7853 (2007), which are herein incorporated by reference for the corresponding discussion). There is only one report that used SERS to detect melamine (Journal of Food Science. 73, 8, 129 (2008), which is herein incorporated by reference for the corresponding discussion). In Lin et al's paper, the SERS detection was achieved through a commercially available substrate, Klarite. However, this commercial substrate does not have very high SERS enhancement, and their study did not give a quantitative relationship between the SERS intensity of melamine peak and the melamine concentration. In order to achieve a reliable and quantitative detection of melamine concentration, one needs not only to distinguish the melamine from complex solution using their unique SERS fingerprint peaks, but also to establish a relationship between the SERS peak intensity and the concentration of the melamine. This requires the production of uniform and reliable SERS substrates. Recently we have found that SERS substrates fabricated by oblique angle deposition (OAD) can provide extremely high SERS enhancement (Appl. Phys. Lett. 87, 031908 (2005); J. Phys. Chem. C. 112, 895 (2008), which are herein incorporated by reference for the corresponding discussion). Those substrates include a tilted silver nanorod array with nanorod diameters of about 100 nm, a tilt angle of about 71° with respect to the surface normal, and a rod density of about 15-25 rods/$\mu m^2$, yielding an enhancement factor of over $10^8$ (Appl. Phys. Lett. 87, 031908 (2005); J. Phys. Chem. C. 112, 895 (2008), which are herein incorporated by reference for the corresponding discussion). The point-to-point detection variation for those substrates is less than 15%, and the substrate can be made into a multi-array chip for high speed screening of analytes (Biosensors and Bioelectronics. 24, 3663 (2009), which is herein incorporated by reference for the corresponding discussion). Our preliminary study shows that this kind of substrate with a shelving life of 3-6 months are ideal for quantitative SERS detection. We have used these substrates to successfully detect and distinguish different viruses, bacteria and their strains, and quantitatively measure different microRNAs and their mixtures (Nano Letters. 6, 2630 (2006); Applied Spectroscopy. 62, 922 (2008); Biosensors and Bioelectronics. 24, 923 (2008); Applied Spectroscopy, 63, 1107-1114 (2009); Optics Express. 15, 19, 12230 (2007), which are herein incorporated by reference for the corresponding discussion).

Here we apply this unique Ag nanorod SERS substrate and multi-well chip to study melamine detection using SERS. Our results show that both the bare substrates and patterned multi-well substrates can be used to quantitatively detect a very low amount of melamine (e.g., 2 pico-grams). This corresponds to an equivalent bulk concentration of 0.1 mg/L in our experiment with a 10 μL droplet, which is lower than the current standard. Through a series of tests, a quantitative relationship between the SERS peak intensities and the melamine concentrations has been established.

Materials and Methods

Preparation of Melamine Sample 100 g melamine (Sigma-Aldrich, St. Louis, Mo.) was weighed with an accuracy of ±0.001 g and was dissolved in 100 mL of 1:1 mixture of methanol and DI water, resulted in a 1000 mg/L concentration of a melamine working stock solution. Methanol was used as a solvent to help promote the sample to spread more uniformly on the AgNR substrates, and to shorten the sample drying time. The working stock was sequentially diluted by the mixture solvent (1:1 v/v water/methanol) into series of concentrations: 100, 80, 60, 40, 20, 10, 8, 6, 4, 2, 1, 0.8, 0.6, 0.4, 0.2, 0.1, and 0.01 mg/L, respectively. Here 1 mg/L is equivalent to 1 ppm. Aliquots of each solution were placed on the AgNR substrates and then the samples were allowed to dry prior to analysis.

Preparation of AgNR Substrates

The AgNR substrates used in this study were fabricated by the oblique angle deposition method (OAD) using a custom-designed electron-beam evaporation system that has been described in detail previously (Appied Spectroscopy 48, 4, 535 (1994); Appl. Phys. Lett. 87, 031908 (2005); J. Phys. Chem. C. 112, 895 (2008), which are herein incorporated by reference for the corresponding discussion). Briefly, the 1 in.×3 in. glass slides (Gold Seal, Portsmouth, N.H.) were used as the starting substrates. Prior to deposition, all the glass slides were cleaned using a Piranha solution. The source materials for evaporation were Ti pellets (Kurt J. Lesker, Clairton, Pa., 99.995%) and Ag pellets (Kurt J. Lesker, Clairton, Pa., 99.999%). Throughout the deposition, the overall thickness of the materials deposited was monitored by a quartz crystal microbalance positioned directly facing the vapor source. A 20 nm-Ti film was first deposited onto the bare glass slide, and a 500 nm Ag film was deposited as the second layer. Then the substrate holder was rotated to 86° with respect to the vapor incident direction, and a layer of ~900 nm long AgNRs was deposited.

Multi-Well SERS Chip Prepared through a Mold-Injection Method

The 1 in.×3 in. AgNR substrates were used to fabricate SERS multi-well chips following previously published procedures (Biosensors and Bioelectronics. 24, 3663 (2009); Proceedings of SPIE. 7321, 732103, 11(2009), which are herein incorporated by reference for the corresponding discussion). This process applied a mold injection method using Polydimethylsiloxane (PDMS), and the resulting SERS chip included 4×10 multi-wells with a sensing area diameter of 3 mm at the bottom of each well. Each well could hold up to ~12.6 μL liquid. After a droplet of 10 μL or sequential droplets of 10 μL of different concentrations of melamine solutions was dispensed and dried, each well was ready for SERS measurement.

SERS Measurement:

Two different sample preparation environments were compared during the dispensing of the melamine solutions on the SERS substrates in this study. A 10 μL droplet of melamine was added on the SERS surface with a pipette either in ambient condition or in a nitrogen glove box. SERS spectra were collected after the droplet on the substrate was dried completely. The SERS spectra were taken by a HRC-10HT Raman Analyzer (Enwave Optronics Inc.). The measurement was conducted using an excitation laser of a wavelength of $\lambda=785$ nm, a power of 25 mW, and a collection time of 10 s. At least five random sampling spots were measured from each well.

Results and Discussion

The Effect of Sample Preparation Environment

Figure 8:
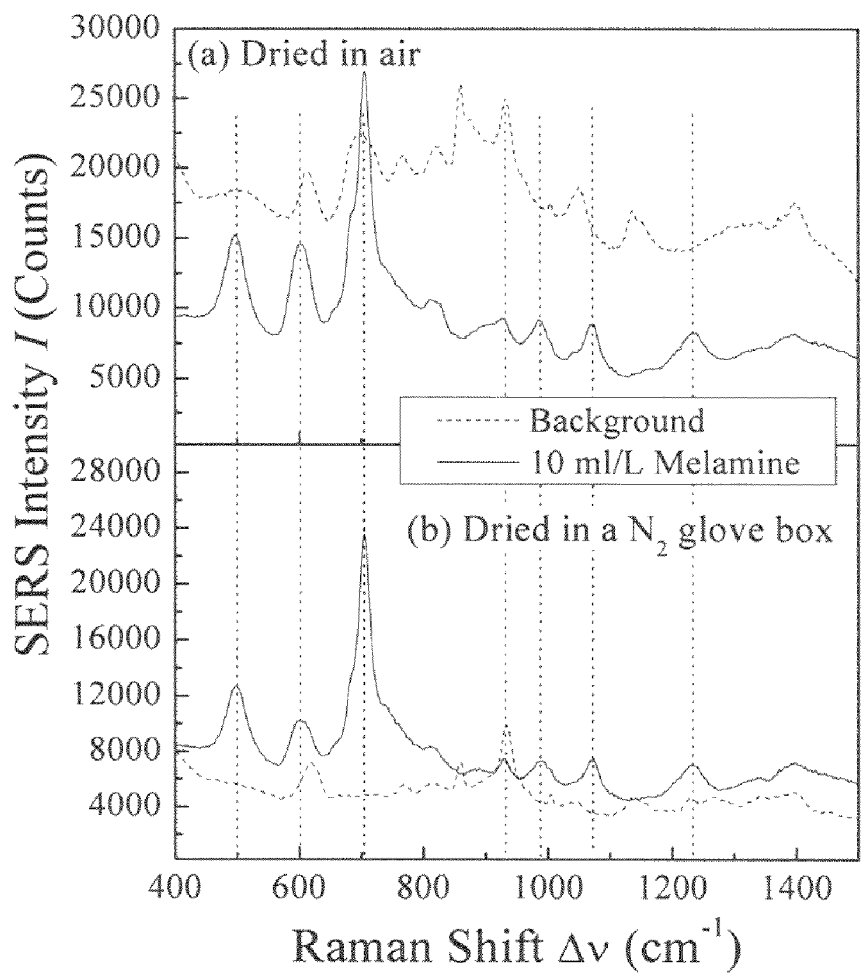
FIGS. 8A-8B are graphs that illustrate the SERS spectra of a 10 μL droplet of 50% methanol (background) and a 10 μL droplet of 10 mg/L melamine dried in SERS wells under (a) the ambient conditions; and in (b) the $N_2$ glove box.

We found that the sample preparation environment had a significant influence on melamine detection. FIG. 8A shows the SERS spectra of 10 μL 50% (v/v) methanol solution (without melamine, labeled as "background") and a 10 μL droplet of 10 mg/L melamine solution dried on a multi-well substrate under ambient conditions. In the 500-1800 $cm^{-1}$ spectral range, there are multiple contamination peaks that appeared in the methanol solution spectrum with high background intensity (>10000 counts). There are some distinguishable differences between the two types of spectra, namely the melamine spectra have sharper and more easily distinguished peaks, compared to that of methanol. However, the two spectra share some common signatures: most of the peak positions overlap and the background signals for both spectra are very high, both of which make differentiating the melamine spectrum difficult. We believe that the high background signals are coming from contamination in air, since according to our measurements, the SERS spectrum measured directly from dry AgNR substrates, shows no peaks (J. Phys. Chem. C. 112, 895 (2008), which is herein incorporated by reference for the corresponding discussion). To confirm our assessment, we have prepared the same samples under a nitrogen glove box (made of Acrylic, Terra's Smart Glovebox™, Terra Universal), and measured the SERS response after the droplets were dried and taken out of the glove box. FIG. 8B shows the SERS spectra of the same samples, i.e., a droplet of 10 μL 50% methanol solution and a droplet of 10 μL 10 mg/L melamine solution dried on a multi-well substrate in a $N_2$ glove box. The SERS spectrum from background has significantly lower intensity compared to that from melamine sample across the entire spectral region, which means the detection signal-to-noise ratio is significantly enhanced. Also, the background signal from the sample prepared in a glove box is significantly smaller than that prepared under ambient condition. However, the overall spectral shape for the two background spectra is the same, which means the contamination is from the same source. We believe for both background samples, the fingerprint SERS peaks are from adsorbed contamination molecules on AgNR substrates in air. Although inside the glove box the environment will not provide additional contamination, the sample still has to be transferred to the glove box under the ambient conditions, and the AgNR substrate could absorb the contaminant molecules during the transport process. For the sample prepared under ambient conditions, however, the AgNR substrate could not only absorb contaminant molecules during exposure to ambient air, but also during the droplet drying process since both substances (water and methanol) are good solvents for many different chemicals. We believe this is why the spectrum from the sample prepared under ambient condition has a five times greater intensity compared to that of samples prepared in a glove box. Thus, in order to have distinguished melamine SERS peaks and better sensitivity, we prepared our samples all in a $N_2$ glove box.

Characteristics of Melamine SERS Spectra

Figure 9:
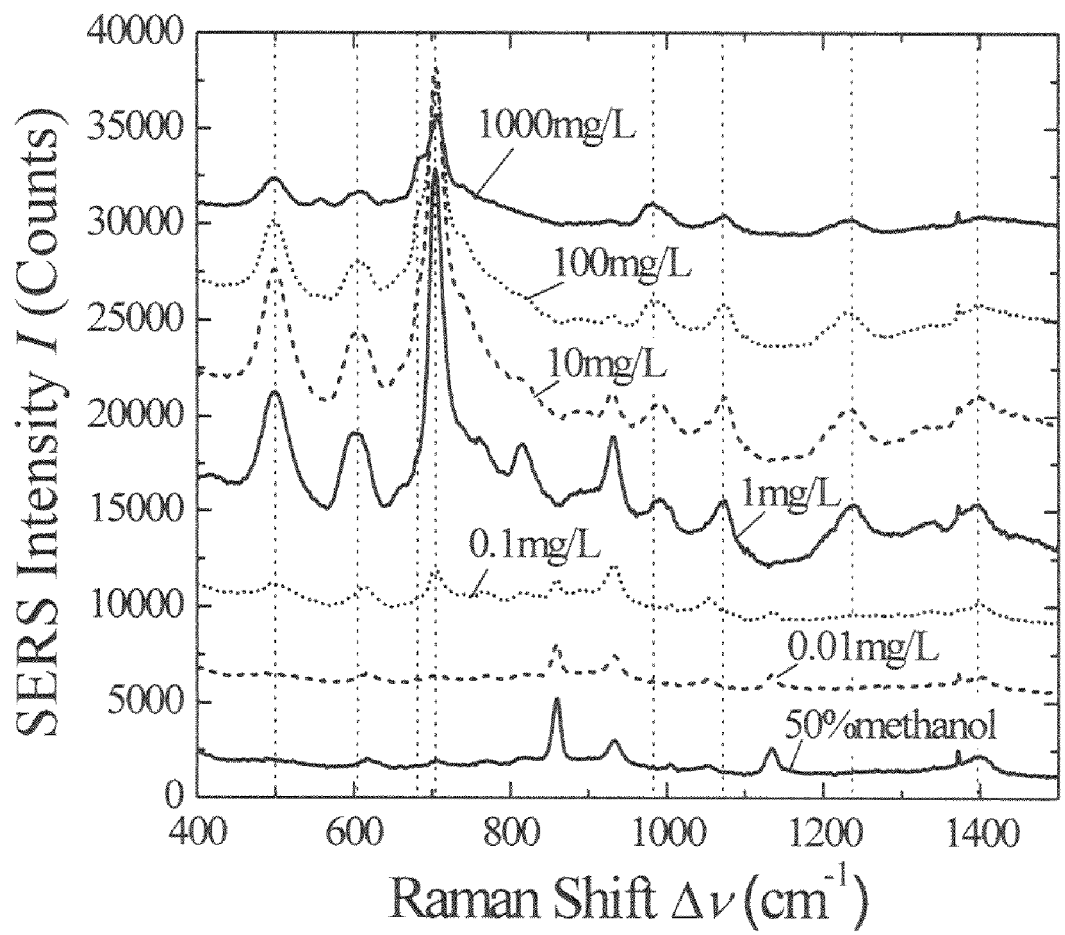
FIG. 9 is a graph that illustrates the average SERS spectra of 10 μL melamine solutions with different concentrations: C=0.01, 0.1, 1, 10, 100, and 1000 mg/L, and the 50% methanol solution.

Most literature reports that the melamine has Raman or SERS peaks between 500 $cm^{-1}$ and 1000 $cm^{-1}$. Table 1 summarized the conventional melamine Raman and SERS peaks reported in the literature and the corresponding vibrational modes. To confirm the SERS characteristic peaks of melamine, we have performed concentration dependent SERS measurements, and only those peaks that change with the melamine concentration can be identified safely as melamine peaks. FIG. 9 shows some representative SERS spectra of melamine at concentrations of 1000, 100, 10, 1, 0.1, and 0.01 mg/L, respectively. To clearly show the spectra for different melamine concentration, we shift the spectra in vertical direction. The background spectrum of 50% methanol water solvent is also shown for comparison. We have observed the following characteristics from FIG. 9: (1) Although both the background and melamine SERS spectra have peaks in 500-1800 $cm^{-1}$ region, some of the peaks do not overlap, especially when the melamine concentration is high (>0.1 mg/L). (2) We have observed the following characteristic peaks varied significantly with the melamine concentration: $\Delta v=498\ cm^{-1}$, $605\ cm^{-1}$, $681\ cm^{-1}$, $704\ cm^{-1}$, $983\ cm^{-1}$, $1070\ cm^{-1}$, $1236\ cm^{-1}$, and $1396\ cm^{-1}$ (all marked by dashed lines in FIG. 9), and they reflect true Raman shift bands for melamine in the 500-1800 $cm^{-1}$ range. The corresponding vibrational modes of those peaks are listed in Table I. (3) The intensities of these peaks change with the melamine concentration. However, these changes are not monotonic. It seems that when melamine concentration increases from 0.1 mg/L to 10 mg/L, the peak intensity increases. With further concentration increase, the SERS peak intensity decreases. The later phenomena may be due to melamine interaction (quenching) at high concentration. (4) One can also notice that when the melamine concentration becomes smaller and smaller, the background peaks appear stronger and stronger. The spectrum of 0.01 mg/L melamine is almost identical to that of the methanol-water background, while the spectrum of 0.1 mg/L melamine still have a few melamine characterization peaks ($\Delta v=498\ cm^{-1}$ and $704\ cm^{-1}$) although the background peaks start to dominate the spectrum. Therefore, we believe that our SERS LOD for melamine is 0.1 mg/L (for a droplet of 10 μL), which is one order lower than the current standard.

Quantitative Relationship Between SERS Peak Intensity and Melamine Concentration For practical analysis, it is very important to establish a quantitative relationship between the SERS spectrum intensity and the melamine concentration. However, SERS detection is a surface based technique, and the SERS intensity is directly related to the number of molecules under laser excitation. Furthermore, the molecules closely bound to the substrate surface will contribute more to the SERS signal than the molecules dispersed throughout the bulk material. In order to establish a direct relationship between the SERS intensity and the bulk concentration of the melamine, one not only needs to know the bulk concentration C, but also needs to know the sample droplet volume V, the number of droplets n, the droplet spreading area A, the diameter of excitation laser beam d. Both parameters V and d can be fixed during the experiments, but the spreading area A depends on the wettability of the liquid if the droplet is spreading on a flat surface (unpatterned substrate). Fortunately, for the multi-well substrate we used, with large enough droplet volume, the spreading area is determined by the diameter of the well D. One could also apply multiple droplets of the same concentration melamine on the same substrate location to enhance the SERS signal. Thus, it is more meaningful to establish a quantitative relationship between the SERS intensity and the mass of melamine m under excitation laser beam. For the multi-well substrate, assuming that the melamine molecules are uniformly spreading on the underlying SERS substrate, the detecting mass of melamine m in the laser spot can be estimated as, $$m=nCVd^2/D^2. \tag{1}$$

In order to obtain a valid melamine mass—SERS intensity relationship, we have performed two different kinds of experiments using the multi-well SERS chip: one is with the fixed melamine solution volume but varying the melamine concentration; and the other is to fix the melamine concentration and the volume of individual sample droplet, but add multiple droplets to a same well in the chip. In our SERS measurements, the laser spot has a diameter d=0.1 mm, each time the dispensed melamine droplet has a volume V=10 μL, and the well has a diameter D=3 mm. For example, if we dispense one droplet of melamine into a well, with melamine concentration C=0.1 mg/L, the detectable mass m≈1 pg; while with C=10 mg/L, m≈1 ng.

Figure 10:
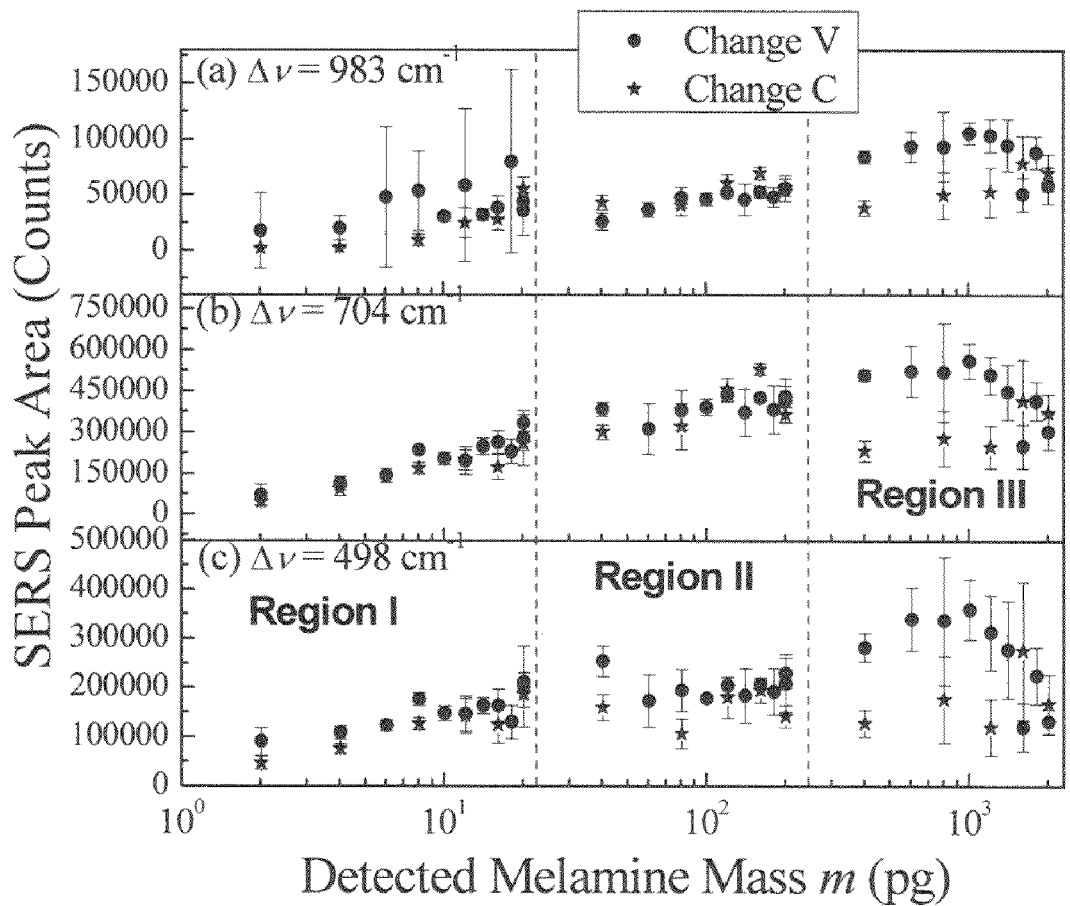
FIG. 10 illustrates the semi-log plot of areal intensity of SERS peak versus detected melamine mass m for (a) Δv=498 cm$^{-1}$, (b) Δv=704 cm$^{-1}$, and (c) Δv=983 cm$^{-1}$, respectively. The 3 regions corresponds to the following experiments: Region I: changing V from 1 μL to 10 μL with a fixed C=1.0 mg/L, or changing C from 0.1 mg/L to 1.0 mg/L with a fixed V=10 μL; Region II: changing V from 1 μL to 10 μL with a fixed C=10 mg/L, or changing C from 2.0 mg/L to 10.0 mg/L with a fixed V=10 μL; Region III: changing V from 1 μL to 10 μL with a fixed C=100 mg/L, or changing C from 20 mg/L to 100 mg/L with a fixed V=10 μL.
Figure 11:
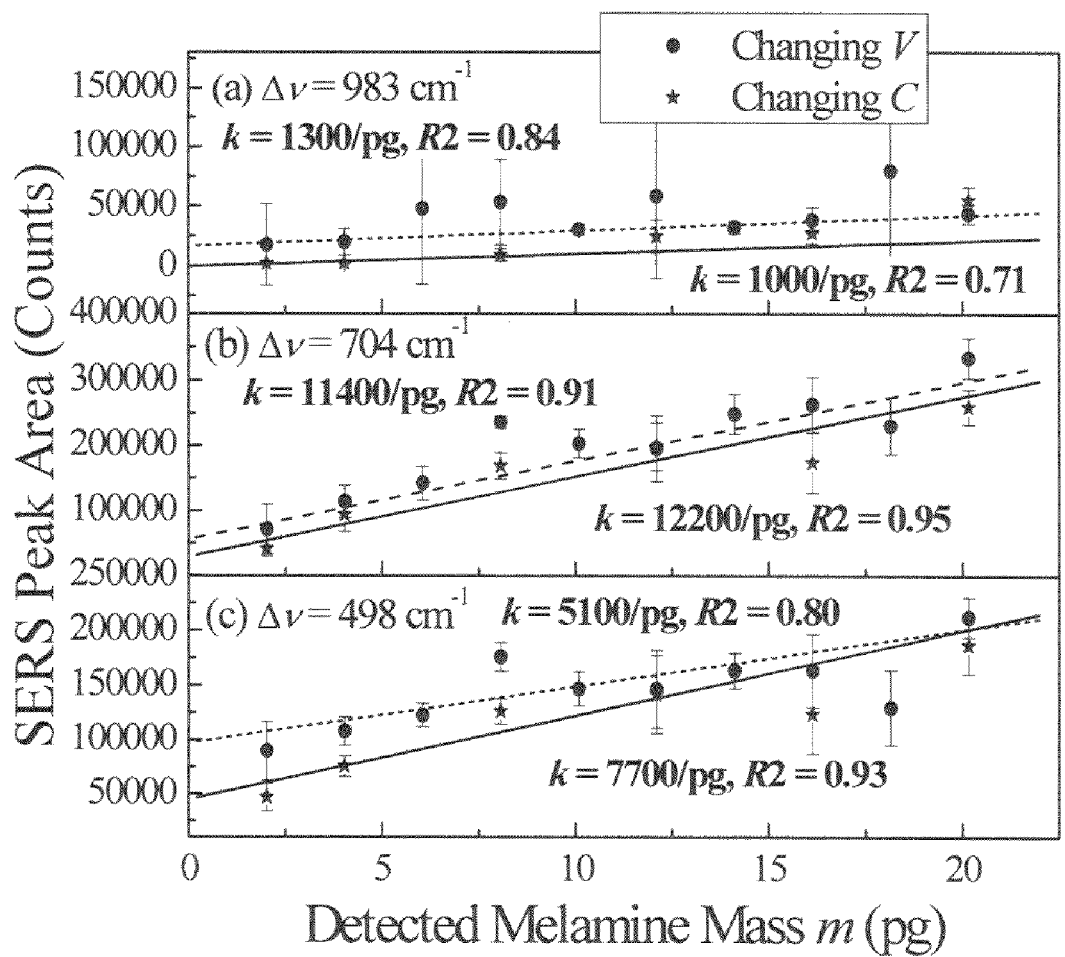
FIG. 11 illustrates the plots of areal intensity of SERS peak and detected melamine mass in low concentration region (Region I in FIG. 10). All the data can be fit by a linear regression, with the regression coefficient of variation R2 varying from 0.71 to 0.95.

To obtain the quantitative relationships, we have selected the three prominent melamine SERS peaks shown in FIG. 9, $\Delta v=498\ cm^{-1}$, $704\ cm^{-1}$, and $983\ cm^{-1}$, and plot their SERS spectral peak areas versus the melamine mass m in a semi-log plot in FIG. 10. The different symbols in FIG. 10 represent different ways to perform the experiments. All three characteristic peaks follow a similar trend with increasing detection mass. The behavior of these peak intensities appears to fall into three distinct regions depending on the mass of melamine m. For Region I, when m increases from 2 pg to 20 pg, the SERS intensity increases monotonically with m. FIG. 11 shows the enlarged plot in this region for m=2 pg to m=20 pg in linear scale. In fact, the SERS peak intensity increases linearly with the melamine mass, and linear fittings show that the slope k varies from 1000 counts/pg to more than 10000 counts/pg, for $\Delta v=498$, 704, and $983\ cm^{-1}$, respectively. The coefficient of variation R2 for the fitting changes from 0.71 to 0.95. If we use the slope k to represent the detection sensitivity, then the $\Delta v=704\ cm^{-1}$ peak gives the most sensitive and uniform response for melamine detection at low concentration, ~10000 counts/pg, and R2 is also larger than 0.9. For a single droplet sampling, this linear region corresponds to C=0.1 mg/L to C=10 mg/L for a fixed V=10 μL. This result shows that using the AgNR SERS substrate, we can detect melamine solution with a concentration of 0.1 mg/L for a fixed V=10 μL. For Region II when m increases from 200 pg to 300 pg, the SERS peak intensity increases gradually; and in Region III when 1000 pg>m>300 pg, the single droplets with varying concentration and multiple droplets with fixed melamine concentration give a reproducible trend. And the SERS intensity starts to decrease when m>1000 pg. Thus, we can claim that the upper limit of our detection is 1000 pg, i.e., the dynamic range of our quantitative SERS detection of melamine is from 2 pg to 1000 pg. For m>1000 pg, since the detection is not consistent for different methods, we can only qualitatively answer whether there is melamine present in the solution or not, i.e., "Yes" or "No" detection.

It is very important for one to realize that for SERS detection, it is the mass or the number of molecules under the excitation laser beam that determines the LOD, not the bulk concentration of the liquid. For our SERS system (including the SERS substrate and SERS equipment), the melamine detection limit is $m_{LOD}=2$ pg. This is the absolute detection limit. In terms of LOD of bulk concentration $C_{LOD}$, from Eq. (1), it is determined by $$C_{LOD} = m_{LOD} \frac{D^2}{nVd^2}.$$

One can push the $C_{LOD}$ below 0.1 mg/L by (1) increasing the sample droplet volume V; (2) increasing the number of droplet applied in the well n; (3) increasing the excitation laser beam size (without changing the laser flux density) d; and (4) decreasing the diameter of the well D. In addition, if one can use a better Raman detection instrument, one can also significantly enhance the detection limit. For example, the current Raman detection system we used is a portable fiber Raman system. The sensitivity of this system is usually one order (or more) of magnitude less than the sensitivity of microRaman system. Thus, we expect that the melamine LOD can be easily reached to 0.2 pg or less if one uses a microRaman system for detection.

Conclusion

In this study, we have used AgNR substrate with a multi-well format to detect pure melamine which is dissolved in 50% methanol by SERS. We have found that as a result of ambient contamination, one needs to prepare the samples inside a $N_2$ glove box. We have identified the characteristic Raman peaks of melamine in the spectral range from 500 cm$^{-1}$ to 1800 cm$^{-1}$. By analyzing three prominent peaks at 498 cm$^{-1}$, 704 cm$^{-1}$, and 983 cm$^{-1}$ using two different sample preparation methods, the single droplet with varying melamine concentration and multi-droplet with fixed melamine concentration, we have established a quantitative relationship between the SERS peak intensities and the mass of melamine under detection. We have found that the LOD is 2 pg, which corresponds to a bulk melamine concentration of 0.1 mg/L for a 10 μL droplet. There is a linear relationship between the detecting melamine mass and the SERS peak area when melamine mass increases from 2 pg to 20 pg, and the upper limit of detection is 1000 pg. Although this current testing method is highly sensitive to a pure melamine solution, there are still many issues associated with the SERS based detections: (1) the contamination issue for the AgNR SERS substrates; this could be inherent to Ag since it has been shown to be easily contaminated with relatively short shelving life, thus Au SERS substrate could be a better choice; (2) the quantitative relationship between the SERS intensity and melamine concentration only exists in a very narrow mass region, which may limit the detection dynamic range; and (3) there are still many practical issues associated with sample separation and purification if one needs to detect melamine in food samples such as milk. There are many background molecules that could greatly interfere with the melamine Raman peaks. Thus, with this proof of concept study for SERS melamine detection, the next urgent task is to find a simple and fast pretreatment method of milk products contaminated with melamine.

TABLE 1

Characteristic Raman and SERS Peaks of Melamine

| Group | | Raman Shift (cm$^{-1}$) |
|---|---|---|
| C=N stretch | | 1680-1620(vs)[a] |
| NH stretch | | 3450-3350(s)[a] |
| —N=C=N— sym stretch | | 1150-1140(vs)[a] |
| —RNH$_2$ | NH$_2$ antisym stretch | 3550-3330(m)[a] |
| | NH$_2$ Sym stretch | 3450-3240(m)[a] |
| | C—N stretch | 1090-1070(m)[a] |
| triazine-ring nitrogen radial in-phase vibration | | 989[b] |
| | | 983[c], 984[d] |
| | | 975[e,f] |
| | | 687[c] |
| | | 682[g] (SERS) |
| | | 676[d] |

[a]Lambert JB, Shurvell HF, Lightner DA, Cooks RG. Organic structural spectroscopy. (Prentice-Hall, New Jersey, 1998), p.196-199.
[b]Yakuphanoglu F, Atalay Y, Erol I. Molecular physics. 103, 24, 3309 (2005).
[c]Marchuwka MK. Acta Chimica Slovenica. 50, 2, 239 (2003).
[d]He L, Yang L, Lin M, Awika J, Ledoux DR, Li H, Mustapha A. Food Quality. 1, 2, 66 (2008).
[e]Gierlinger N, Hansmann C, Roder T, Sixta H, Gindl W, Wimmer R. Holzforschung. 59, 2, 210 (2005).
[f]Thomas R, Herbert S. Lenzinger Berichte. 83, 13 (2004).
[g]Lin M, He L, Awika L, Yang L, Ledoux DR, Li H, Mustapha A. Journal of Food Science. 73, 8, 129 (2008).

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are merely set forth for a clear understanding of the principles of the disclosure. Many variations and modifications may be made to the above-described embodiments. All such modifications and variations are intended to be included herein within the scope of this disclosure and protected by the following claims.

Therefore, at least the following is claimed:

1. A method of detecting melamine in a sample comprising:
    providing a surface enhanced Raman spectroscopy (SERS) substrate, wherein the SERS substrate comprises a Ag nanorod array substrate, wherein an angle, β, is formed between the nanorods and the SERS substrate, and wherein the angle is about 30° to 75°;
    exposing the sample to the SERS substrate; and
    obtaining a unique SERS spectrum for the melamine, wherein the SERS substrate comprises a multi-well array substrate, wherein the multi-well array substrate comprises at least one well, wherein the well has a bottom surface and a side surface, and wherein a plurality of nanorod structures are disposed on the bottom surface, wherein the plurality of nanorod structures comprise Ag nanorod structures, wherein the side surface is made of a material selected from the group consisting of: polydimethylsiloxane (PDMS), fluorinated PDMS, poly(methyl methacrylate) (PMMA), polycyclic olefin polyethylene copolymers, polycarbonate, polyalkanes, polyacrylate polybutanol co-polymers, polystyrenes, polyionomers, polybutyl terephthalate (PBT), polyamides, polyoxymethylene (POM), other acetyl resins, and a combination thereof, and the bottom surface is made of a silicon material.

2. The method of claim 1, wherein the Ag nanorod array substrate is fabricated by oblique angle deposition (OAD).

3. The method of claim 1, wherein the nanorods are about 900 nm long.

4. The method of claim 1, wherein the nanorods have a diameter of about 110 nm.

5. The method of claim 1, wherein the nanorod density is about 15-25 rods/$\mu m^2$.

6. The method of claim 1, wherein the wells are a shape selected from the group consisting of: a cylindrical shape, a conical shape, a polygonal shape, and a combination thereof.

7. The method of claim 1, wherein the wells comprise a sensing area diameter of about 3 mm at the bottom of each well.

8. The method of claim 1, wherein the nanorods are about 10 to 5000 nm long.

9. The method of claim 1, wherein the nanorods have a diameter of about 10 to 150 nm.

10. The method of claim 1, wherein the nanorod density is about 11-2500 rods/$\mu m^2$.

11. A method of detecting and quantifying melamine in a sample comprising: providing a surface enhanced Raman spectroscopy (SERS) substrate, wherein the SERS substrate comprises a Ag nanorod array substrate, wherein an angle, $\beta$, is formed between the nanorods and the SERS substrate, and wherein the angle is about 30° to 75°;

exposing the sample to the SERS substrate;

obtaining a unique SERS spectrum for the melamine; and analyzing the unique SERS spectrum to quantify the melamine, wherein the SERS substrate comprises a multi-well array substrate, wherein the multi-well array substrate comprises at least one well, wherein the well has a bottom surface and a side surface, and wherein a plurality of nanorod structures are disposed on the bottom surface, wherein the side surface is made of a material selected from the group consisting of: polydimethylsiloxane (PDMS), fluorinated PDMS, poly(methyl methacrylate) (PMMA), polycyclic olefin polyethylene copolymers, polycarbonate, polyalkanes, polyacrylate polybutanol co-polymers, polystyrenes, polyionomers, polybutyl terephthalate (PBT), polyamides, polyoxymethylene (POM), other acetyl resins, and a combination thereof and the bottom surface is made of a silicon material.

12. The method of claim 11, wherein the wells are a shape selected from the group consisting of: a cylindrical shape, a conical shape, a polygonal shape, and a combination thereof.

13. The method of claim 11, wherein the nanorods are about 10 to 5000 nm long.

14. The method of claim 11, wherein the nanorods have a diameter of about 10 to 150 nm.

15. The method of claim 11, wherein the nanorod density is about 11-2500 rods/$\mu m^2$.

\* \* \* \* \*